United States Patent [19]

Marconet

[11] Patent Number: 5,480,212
[45] Date of Patent: Jan. 2, 1996

[54] MEDICAL INSTRUMENT POSITIONER AND PATIENT SUPPORT APPARATUS

[75] Inventor: Robert E. Marconet, Cincinnati, Ohio

[73] Assignee: Reliance Medical Products, Inc., Mason, Ohio

[21] Appl. No.: 154,854

[22] Filed: Nov. 18, 1993

[51] Int. Cl.$^6$ ...................................................... A47C 7/62
[52] U.S. Cl. ............................ 297/188.01; 297/188.1; 297/241; 248/124.1; 248/280.11; 248/281.11; 5/503.1; 5/658
[58] Field of Search ........................... 297/188.01, 188.1, 297/188.08, 188.21, 241; 248/124, 122, 349, 280.1, 281.1; 5/503.1, 658, 507.1

[56] References Cited

U.S. PATENT DOCUMENTS

| | | |
|---|---|---|
| 1,653,772 | 1/1926 | Knoche . |
| 2,297,845 | 10/1942 | Templeton, Jr. .................... 297/241 X |
| 2,424,729 | 7/1947 | Andreasen ......................... 297/241 X |
| 2,681,690 | 6/1954 | Johnson et al. ......................... 297/241 |
| 2,696,963 | 12/1954 | Shepherd .............................. 5/503.1 X |
| 2,950,836 | 8/1960 | Murdock . |
| 3,151,910 | 10/1964 | Carson ........................... 297/188.01 X |
| 3,222,105 | 12/1965 | Cross . |
| 3,259,428 | 7/1966 | Wenger et al. . |
| 3,524,676 | 8/1970 | Cocherell et al. . |
| 3,601,443 | 8/1971 | Jones . |
| 3,712,669 | 1/1973 | Cates . |
| 4,136,908 | 1/1979 | Crayne . |
| 4,397,439 | 8/1983 | Wilbur et al. . |
| 4,427,382 | 1/1984 | Hoffmeister et al. . |
| 4,500,134 | 2/1985 | Kaneko et al. . |
| 4,572,536 | 2/1986 | Doughty . |

Primary Examiner—Laurie K. Cranmer
Attorney, Agent, or Firm—Wood, Herron & Evans

[57] ABSTRACT

A medical instrument positioner including a lever arm pivotally secured at a first end to a stationary base, which is preferably the base of a patient support such as an examination chair, and including a pole extending upwardly from a second end as well as a lockable caster secured to the second end for providing rolling but selectively lockable support of the positioner with respect to the base. The patient support provides a heavy, stable object for counteracting the moment created by, for example, a microscope and microscope mounting arm attached to the upper end of the vertical pole. The microscope mounting arm preferably takes the form of a linkage assembly secured to the upper end of the pole. The microscope mounting arm receives the microscope for allowing precise adjustment of the microscope orientation with respect to the patient.

17 Claims, 2 Drawing Sheets

MEDICAL INSTRUMENT POSITIONER AND PATIENT SUPPORT APPARATUS

BACKGROUND OF THE INVENTION

The present invention generally relates to medical instrument positioners for use during surgical or examination procedures and, more specifically, to a microscope positioner pivotally connected to a patient support such as a lift and recline chair.

Microscopes are increasingly being used to perform delicate surgical procedures such as radial keratotomy (RK) procedures. During such procedures, the surgeon must be able to accurately and securely position the microscope over the surgical site such as over the patient's eye during an RK procedure. In addition, it is very desirable for the surgeon to also be able to move the microscope away from the surgical site and then quickly, accurately and securely back over the site as necessary before, during and/or after the surgical procedure.

Past support apparatus for surgical microscopes have included fixed supports in which an adjustable mounting arm having a microscope attached at an outer end thereof is fixedly mounted adjacent the patient. Unfortunately, many times such fixed support of the microscope assembly does not provide the surgeon with enough mobility and flexibility when positioning the microscope with respect to the examination chair and the patient. Moreover, the fixed support base, e.g., an adjacent table or stand for the microscope mounting arm, must be sufficiently stable and/or heavy to withstand and counteract the moment created by the mounting arm and the relatively heavy microscope attached at the outer end thereof. Finally, fixed supports limit the locations at which the examination chair may be placed within the examination room.

A supporting apparatus including a vertical pole riding on a base supported by casters, much like an I.V. pole, has also been used to support a microscope and an adjustable mounting arm attached at an upper end thereof. In this apparatus the mounting arm for the microscope is attached to the upper end of the pole and the relatively heavy microscope is attached at an outer end of the mounting arm. One disadvantage of this type of support is that the multiple caster supported base of the apparatus must be formed as a cumbersome, bulky unit to provide enough support to counteract the moment created by both the mounting arm and the microscope. Another disadvantage is that the bulky base takes up a large amount of space in the examination room. Finally, the rolling vertical pole is not quickly and accurately positionable with respect to the examination chair and the patient. In this regard, the casters at the base of the pole allow the pole to be moved in any direction and therefore positioning the pole with respect to the patient is awkward.

SUMMARY OF THE INVENTION

The present invention provides a medical instrument positioner comprising a lever arm secured at a first end to a stationary base such that it may pivot about a vertical axis. The stationary base is preferably the base of a patient support such as an examination chair, and including a support pole extending upwardly from a second end. A lockable caster is also secured to the second end for providing rolling but selectively lockable support of the lever arm and the pole with respect to the base. The lever arm is also pivotal about a horizontal axis to allow vertical movement of the second end with respect to the first end and to ensure that rolling contact is maintained between the castor and support surface such as the floor of an examination room.

In the preferred embodiment, the positioner is adapted specifically for use with a surgical microscope. An adjustable microscope mounting arm and attached microscope are connected to the upper end of the pole. The caster provides rolling support along the floor as the lever arm, pole, microscope mount and microscope are moved along an arc adjacent the patient support. The arc preferably extends through a path of approximately 270° but may be more or less than this depending on the needs of specific applications. The patient support provides a heavy, stable object for counteracting the moment created by the microscope mounting arm and microscope attached to the upper end of the vertical pole. The microscope mounting arm preferably takes the form of an adjustable linkage assembly and includes a microscope mount which adjustably receives the microscope for allowing precise adjustment of the microscope orientation with respect to the patient.

The medical instrument positioner of the present invention allows a medical diagnostic or surgical instrument to be very quickly and accurately positioned and repositioned with respect to a patient lying on a support such as an examination chair. As mentioned above, the preferred embodiment of the invention is directed to the use of the medical instrument positioner for mounting a surgical microscope. In this regard, when the doctor or other medical professional involved with performing an operation or examination of the patient desires to move the microscope away from the patient, he needs only to unlock the caster using their foot, swing the positioner into a new position and again lock the caster. Then, when the microscope is again needed in position over the surgical or examination site of the same patient or a different patient, the caster is again quickly unlocked and the positioner is swung to the original location where the doctor again locks the caster to fix the positioner and microscope with respect to the patient.

Further advantages of the present invention stem, for example, from the combination of the medical instrument positioner with a patient support such as an examination chair. More specifically, since the heavy patient support or chair counteracts the moment created by the medical instrument, such as a relatively heavy surgical microscope, as well as its adjustable mounting arm, there is no need for a separate, bulky base for providing such support. As a result of the compact, efficient design of the positioner in combination with a patient support, there is significant saving of space in the examination room. Moreover, the positioner of the present invention is always positioned in a fixed relationship with respect to the patient support since it is preferably attached directly to the base thereof. There is no separate base to move and position with respect to the patient support. The present invention further provides more flexibility in creating the layout of the examination room as the patient support or chair and attached positioner are located within the room as one unit. For example, the patient support or chair need not be located adjacent a separate table or stand acting as a support base as do some fixed supports of the past.

Other features and advantages of the present invention will become more readily apparent to those of ordinary skill in the art upon review of the following detailed description taken in conjunction with the accompanying drawings.

DETAILED DESCRIPTION OF THE PREFERRED EMBODIMENT

Figure 1:
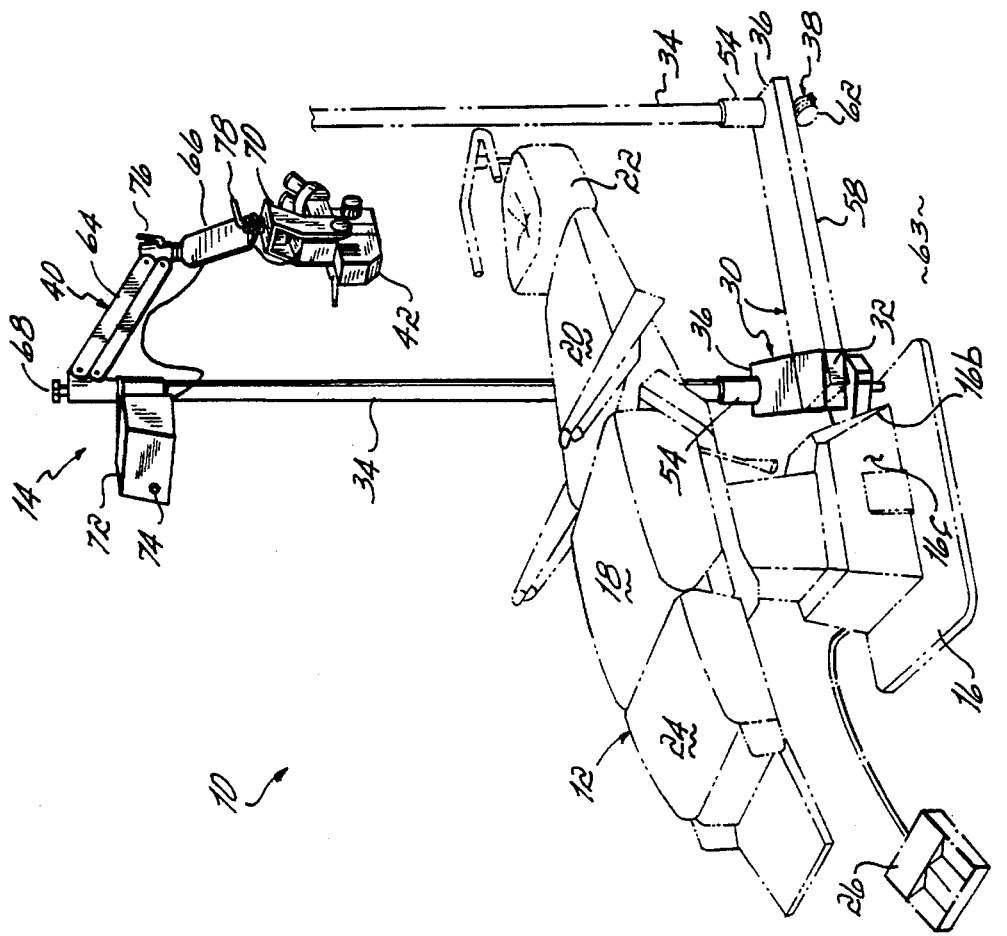
FIG. 1 is a perspective view of the medical instrument positioner of the present invention secured to an examination chair.

A combined patient support and medical instrument positioner 10 is illustrated in FIG. 1 and includes a patient support 12 which, in the preferred embodiment, is a lift and recline chair with a medical instrument positioner 14 of the present invention secured thereto. While the patient support 12 is shown and described herein as being a lift and recline examination chair, it will be appreciated that the patient support 12 may take other forms such as an examination table or bed. The lift and recline chair 12 is conventional in form and includes a fixed support base 16, a seat portion 18, a back portion 20 connected to one side of the seat portion 18, a head rest portion 22 connected to the back portion 20, and a leg rest portion 24 attached to the opposite side of the seat portion 18 from the back portion 20. The seat portion 18 is connected to the base 16 and is vertically moveable with respect thereto in a conventional manner using, for example, a hydraulic lift mechanism operated by a foot switch 26. As is also conventional, the back portion 20 is angularly adjustable with respect to the seat portion 18 by means of the same foot switch 26 to allow a patient to be reclined in the chair 12.

As further shown in FIG. 1, the positioner 14 generally comprises a lever arm 30 pivotally connected at a first end 32 to the base 16 of the patient support or chair 12. A vertically oriented pole 34 extends upwardly from a second end 36 of the lever arm 30, A lockable caster 38 is attached at the second end 36 of the lever arm 30 for providing rolling support of the microscope positioner 14 on the floor 63 of an examination or operating room as it is pivoted about the first end 32, In this regard, the caster 38 will roll on the floor 63 on which the base 16 sits and will travel through a predetermined arc as will be described further below. As also detailed below, a medical instrument mounting arm, which in the preferred embodiment takes the form of a microscope mounting arm 40, is secured to the upper end of the pole 34. A microscope 42 is attached at the outer end of the mounting arm 40.

Figure 2:
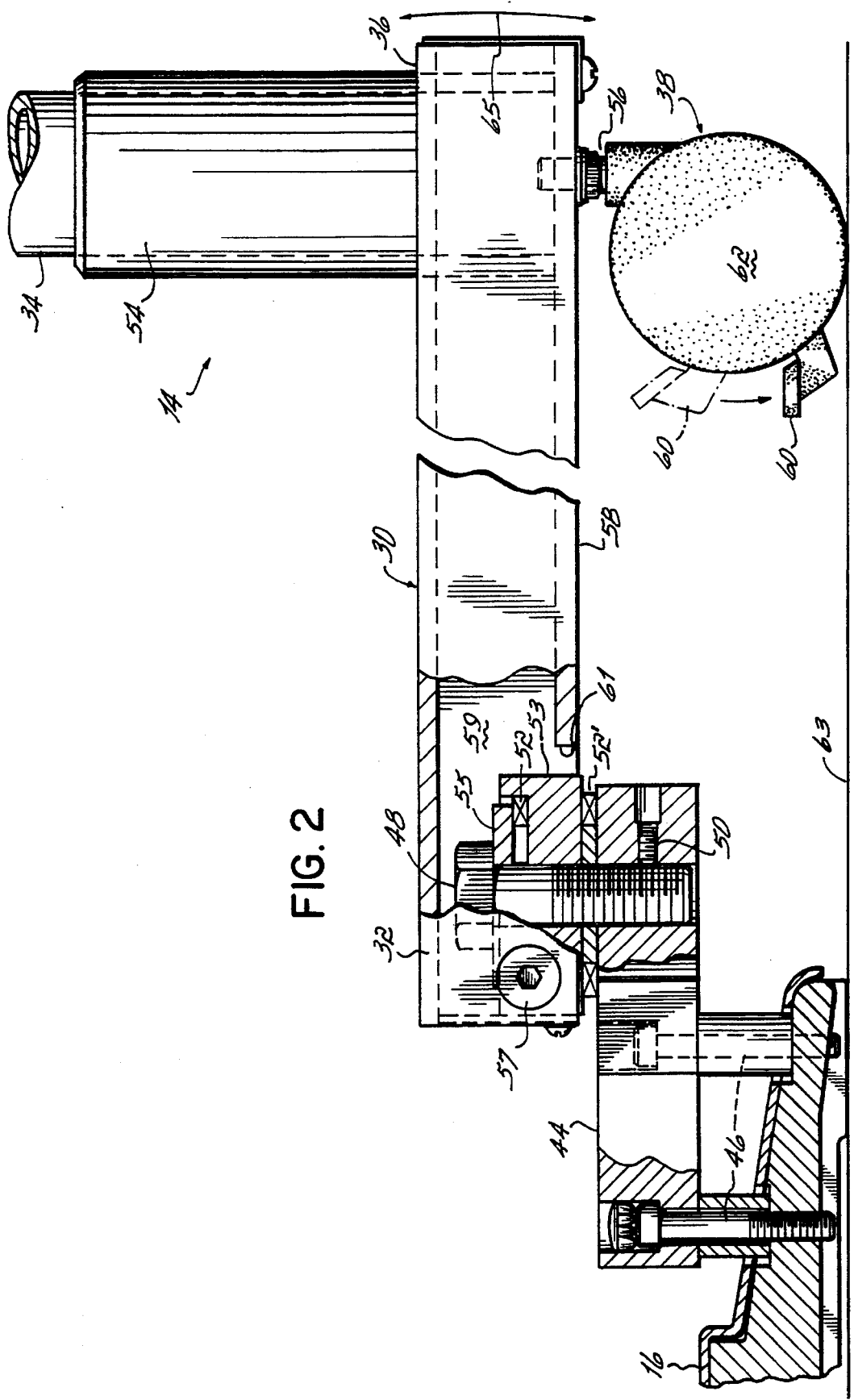
FIG. 2 is a partial cross sectional view of the lower end of the positioner of FIG. 1 and its pivotal attachment to the base of the examination chair; and, FIG. 3 is a diagrammatic top view of the positioner of FIG. 1 showing the range of movement thereof with respect to the base of the examination chair.

As further detailed in FIG. 2, the lever arm 30 is pivotally secured at its first end 32 to a base plate 44 which, in turn, is rigidly secured to the base 16 of the patient support or chair 12 by way of screws 46. The lever arm 30 is secured to the base plate 44 by a bolt 48 fixed to the base plate 44 by a set screw 50. The bolt 48 further secures a pair of thrust bearings 52, 52' on either side of the pivot block 53 to allow relative pivotal motion of the pivot block 53 and attached lever arm 30 with respect to the fixed base plate 44 about a vertical axis defined by the axis of the bolt 48. Bolt 48 secures an upper bearing 52 against pivot block 53 by way of a washer 55 and secures a second bearing 52' between the pivot block 53 and base plate 44. The vertical pole 34 is fixed within a hollow support tube 54 by way of set screws (not shown). The hollow support tube 54 is rigidly fixed to the second end 36 of the lever arm 30 in a suitable manner such as by welding.

The lever arm 30 is further pivotally secured at its first end 32 to pivot about a horizontal axis defined by the axis of a pair of screws 57, only one of which is shown in FIG. 2. The screws 57 have coincident axes and are each rigidly secured into pivot block 55 as by set screws (not shown). A slight clearance gap is left between each screw 57 and the holes through which they extend in the arm 30 to allow pivoting of arm 30 and vertical movement of the second end 36 of the arm 30 in the direction of arrow 65. Thus, as will be appreciated from FIG. 2, as the castor 38 rolls along floor 63, the castor 38 will move up and down with respect to the base 16 and base plate 44 and will thereby compensate for any irregularities in the floor surface 63 or in the machining of the base 16. In other words, rolling contact will be maintained so as to minimize shake or chatter of the positioner 14 as castor 38 rotates and maximizes stability of the positioner 14 as it is moved about and when it is fixed in place. Pivoting of arm 30 about screws 57 causes movement of the pivot block 52 slightly into and out of the hollow interior 59 of arm 30 by way of an opening 61 in the bottom thereof. The angular range of movement of the arm 30 about screws 57 is about ±5°.

The lockable caster 38 is a conventional caster sold, for example, by Gross Stabil Corp. under Part No. D2BF375-3. The caster swivels about a stem 56 which is secured to the underside or lower surface 58 of the lever arm 32. A foot operated lock mechanism 60 is provided on the caster 38 and enables selective locking of the rolling movement of the caster wheel 62 along the floor 63. Thus, when the locking mechanism 60 is moved from the position shown in phantom in FIG. 2 to the position shown in solid lines, the caster wheel 62 cannot rotate and thus the lever arm 30 is effectively locked in a desired position with respect to the patient support or chair 12 as shown in FIG. 1.

Figure 3:
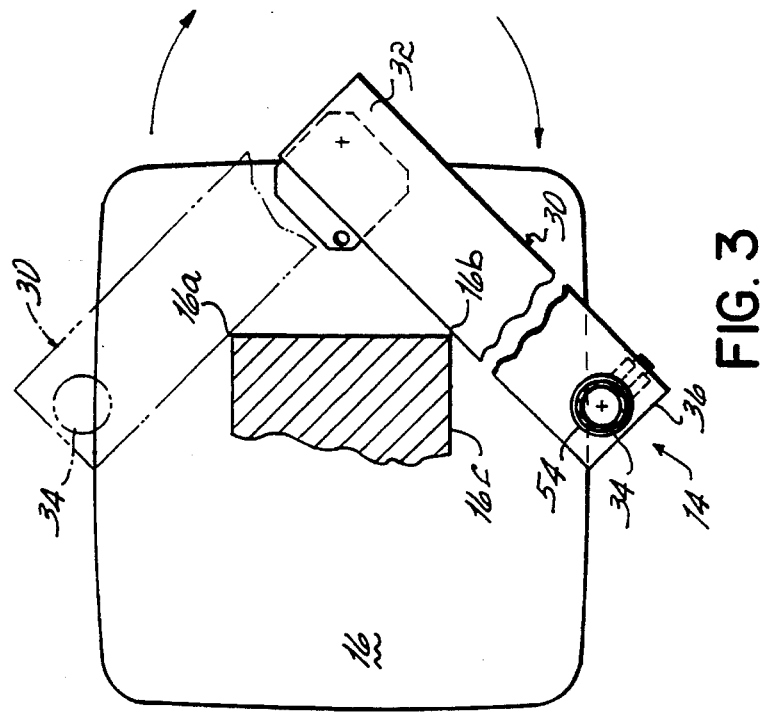

FIG. 3 illustrates the range of angular movement of the medical instrument positioner 14 with respect to the base 16 of the patient support or chair 12. Preferably, the positioner 14 will have an angular range of movement of at least 90°. More preferably, and as shown in FIG. 3, the lever arm 30 will stop at limits which are disposed approximately 270° apart and are defined by two points 16a, 16b at which the lever arm 30 abuts against a portion 16c of the base 16.

As best illustrated in FIG. 1, when the patient support is a lift and recline chair as shown, the lever arm 30 will be of sufficient length to allow movement of the vertical pole 34 along an arc from one side of the chair 12 to the other without interference from the headrest 22 when the chair is in a reclined position and, most preferably, when the chair is in a fully reclined position as shown. This is illustrated schematically in FIG. 1 with the positioner 14 being moved between the position shown in solid lines and the position shown in phantom. If necessary, a support bar may be rigidly connected at an angle between the lever arm 30 and pole 34 for added support and stability of the pole 34.

As further shown in FIG. 1, the microscope mounting arm 40 may be comprised of any one of numerous such conventional microscope mounting arms but is preferably of the variety sold by Moller-Wedel under Part No. 613 208. As shown, this microscope mounting arm 40 comprises a pair of adjustably connected linkage arms 64, 66. Linkage arm 64 is rotatably secured to the upper end of the vertical pole and may be selectively locked and unlocked for rotational movement with respect thereto by tightening and untightening a locking knob 68. Linkage arm 66 includes a microscope mount 70 adjustably rotatably secured to the outer end thereof. A control box 72 is also mounted to the vertical pole and includes a knob 74 which controls the light intensity of the microscope 42. The linkage arms 64, 66 as well as the microscope mount 70 allow multi-directional, precise adjustment of the microscope position with respect to a patient lying on the patient support or chair 12. In this regard, tightening and untightening lever 76 allows selectively lockable rotation of linkage arm 66 with respect to linkage arm 64 while tightening and untightening lever 78 allows selectively lockable rotation of the microscope mount 70 with respect to the linkage arm 66.

As shown in FIG. 1, the microscope 42 is positioned over the headrest 22 of the patient support or chair 12 so as to, for example, allow a surgeon to perform an RK procedure on the eyes of a patient. The adjustable microscope mounting arm 40 allows precise positioning of the microscope 42 over the patient. As will further be readily appreciated, the caster 38 is easily unlocked by the surgeon's foot to allow the positioner 14 and attached microscope mounting arm 40 and microscope 42 to easily be moved out of the doctor's and/or the patient's way at any time before, during, or after a surgical procedure. The lockable caster 38 may then again be locked to maintain the positioner 14 out of the way. When the microscope 42 is again needed over the surgical site, such as over the patient's head in this case, the lockable caster 38 is simply unlocked and the positioner 14 is again moved back to the original position. The surgeon then simply steps on the locking mechanism 60 of the caster 38 to effectively lock the positioner 14 and attached microscope 42 in the original position. Precise positioning may then be accomplished, if necessary, by way of the adjustable microscope mounting arm 40.

Although a preferred embodiment of the present invention has been fully detailed herein, the artisan of ordinary skill will readily recognize further modifications and substitutions to the invention which do not depart from the inventive concepts disclosed herein. For example, although the present invention has been described in connection with the positioning of a microscope over a surgical or examination site, it will be appreciated that other diagnostic or medical treatment apparatus may easily be substituted in place of a microscope, depending on the particular needs of the operator, while still obtaining the benefits and advantages of the positioner of the present invention. Still further modifications will become apparent to those of ordinary skill and applicant therefore intends to be bound only by the scope of the claims appended hereto.

I claim:

1. A patient support in combination with a medical instrument positioner comprising:

a support having at least one surface for supporting a patient undergoing a medical examination or medical procedure, said support including a fixed support base, and a medical instrument positioner comprising:

a lever arm having first and second ends, said first end including a pivotal connection to said support base;

a pole attached to said second end and extending upwardly therefrom, said pole including means at an upper end thereof for attaching a medical instrument mounting arm and a medical instrument thereto; and, a lockable caster attached to said lever arm at said second end for supporting said lever arm and said pole on a support surface while allowing rolling pivotal movement thereof with respect to said base by way of said pivot connection, said caster being selectively lockable to stop said rolling pivotal movement.

2. The patient support and medical instrument positioner of claim 1 wherein said lever arm has an angular range of motion of at least 90° with respect to said base.

3. The patient support and medical instrument positioner of claim 1 wherein said first end of said lever arm is connected to a rear portion of said base proximate a headrest portion of said patient support, wherein said lever arm has an angular range of motion sufficient to move said pole from one side of said patient support to another.

4. The patient support and medical instrument positioner of claim 1 further comprising a microscope mounting arm assembly connected at said upper end of said pole.

5. The patient support and medical instrument positioner of claim 4 wherein said microscope mounting arm assembly is connected for selectively lockable rotation about said pole.

6. The patient support and medical instrument positioner of claim 5 wherein said microscope mounting arm assembly comprises a pair of pivotally connected linkage arms having a microscope mount connected on an outer end thereof, wherein said linkage arms and said microscope mount allow precise adjustment of the orientation of a microscope received in said microscope mount.

7. The patient support and medical instrument positioner of claim 1 wherein said patient support is an adjustable chair including a seat portion connected to said fixed support base and being vertically adjustable with respect to said base and further including a back portion connected to said seat portion and being angularly adjustable with respect to said seat portion.

8. The patient support and medical instrument positioner of claim 7 wherein said lever arm is of sufficient length to allow said pole to be moved from one side of said chair back portion to the other while said chair back portion is in a reclined position.

9. The patient support and medical instrument positioner of claim 8 wherein said lever arm is of sufficient length to allow said pole to be moved from one side of said chair back portion to the other while said chair back portion is in a fully reclined position.

10. The patient support and medical instrument positioner of claim 1 wherein said lockable caster is attached to a lower surface of said lever arm.

11. The patient support and medical instrument positioner of claim 1 wherein said first end of said lever arm is further pivotally secured to said support base to allow vertical movement of said second end with respect to said first end.

12. A medical instrument positioner comprising:

a lever arm having first and second ends, said first end including a pivot connection to a fixed base;

a pole attached to said second end and extending upwardly therefrom, said pole including means at an upper end thereof for attaching a medical instrument mounting arm and a medical instrument thereto; and, a lockable caster attached to said lever arm at said second end for supporting said lever arm and said pole on a support surface while allowing rolling pivotal movement thereof with respect to said fixed base by way of said pivot connection, said caster being selectively lockable to stop said rolling pivotal movement.

13. The medical instrument positioner of claim 12 wherein said lever arm has an angular range of motion of at least 90° with respect to said base.

14. The medical instrument positioner of claim 12 further comprising a microscope mounting arm assembly connected at said upper end of said pole.

15. The medical instrument positioner of claim 14 wherein said microscope mounting arm assembly is connected for selectively lockable rotation about said pole.

16. The medical instrument positioner of claim 15 wherein said microscope mounting arm assembly comprises a pair of pivotally connected linkage arms having a microscope mount connected on an outer end thereof, wherein said linkage arms and said microscope mount allow precise adjustment of the orientation of a microscope received in said microscope mount.

17. The medical instrument positioner of claim 12 wherein said first end of said lever arm is further pivotally secured to said base to allow vertical movement of said second end with respect to said first end.

* * * * *